(12) United States Patent
Marsh et al.

(10) Patent No.: US 7,977,301 B2
(45) Date of Patent: Jul. 12, 2011

(54) WET WIPE LOTIONS COMPRISING PARTICULATE MATERIAL

(75) Inventors: Randall Glenn Marsh, West Chester, OH (US); Lee Ellen Drechsler, Cincinnati, OH (US); Mathias Kurt Herrlein, Hofheim (DE); Antonio Martinez Campoy, Rüsselsheim (DE); Mary Rebecca Zimnawoda, West Lafayette, IN (US); Philip Andrew Sawin, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 12/683,487

(22) Filed: Jan. 7, 2010

(65) Prior Publication Data
US 2010/0105593 A1    Apr. 29, 2010

Related U.S. Application Data

(63) Continuation of application No. 10/941,206, filed on Sep. 15, 2004, now Pat. No. 7,666,827.

(51) Int. Cl.
*A61K 7/50* (2006.01)

(52) U.S. Cl. ......... 510/439; 510/426; 510/463; 424/401

(58) Field of Classification Search .................. None
See application file for complete search history.

(56) References Cited

U.S. PATENT DOCUMENTS

| 4,904,524 A | 2/1990 | Yoh |
| 4,980,176 A | 12/1990 | Berke et al. |
| 5,041,457 A | 8/1991 | Hsu |
| 5,332,118 A | 7/1994 | Muckenfuhs |
| 5,428,050 A | 6/1995 | Merianos |
| 5,496,842 A | 3/1996 | Merianos |
| 5,552,425 A | 9/1996 | Merianos |
| 5,631,273 A | 5/1997 | Merianos |
| 5,965,594 A | 10/1999 | Schoenberg et al. |
| 6,143,204 A | 11/2000 | Lutz et al. |
| 6,764,988 B2 | 7/2004 | Koenig et al. |
| 2002/0122832 A1 | 9/2002 | Hanke et al. |
| 2002/0172656 A1* | 11/2002 | Biedermann et al. ...... 424/70.21 |
| 2003/0039580 A1 | 2/2003 | Borokhov et al. |
| 2005/0002978 A1* | 1/2005 | Crook et al. .................. 424/401 |
| 2005/0009431 A1* | 1/2005 | Chamba et al. ............... 442/234 |

FOREIGN PATENT DOCUMENTS

| EP | 0 950 391 A1 | 10/1999 |
| EP | 1 405 632 A | 4/2004 |
| EP | 1 493 429 | 1/2005 |
| JP | 3167300 B2 | 5/2001 |
| WO | WO 98/06404 A1 | 2/1998 |
| WO | WO 03/005874 A | 1/2003 |

OTHER PUBLICATIONS

PCT Search Report, mailed Feb. 3, 2006, 4 pages.

* cited by examiner

*Primary Examiner* — Necholus Ogden, Jr.
(74) *Attorney, Agent, or Firm* — Richard L. Alexander; Amy M. Foust

(57) ABSTRACT

The present invention provides a wet wipe made up of a substrate impregnated with a cleaning lotion where the cleaning lotion includes a particulate material.

20 Claims, 2 Drawing Sheets

FIG. 2
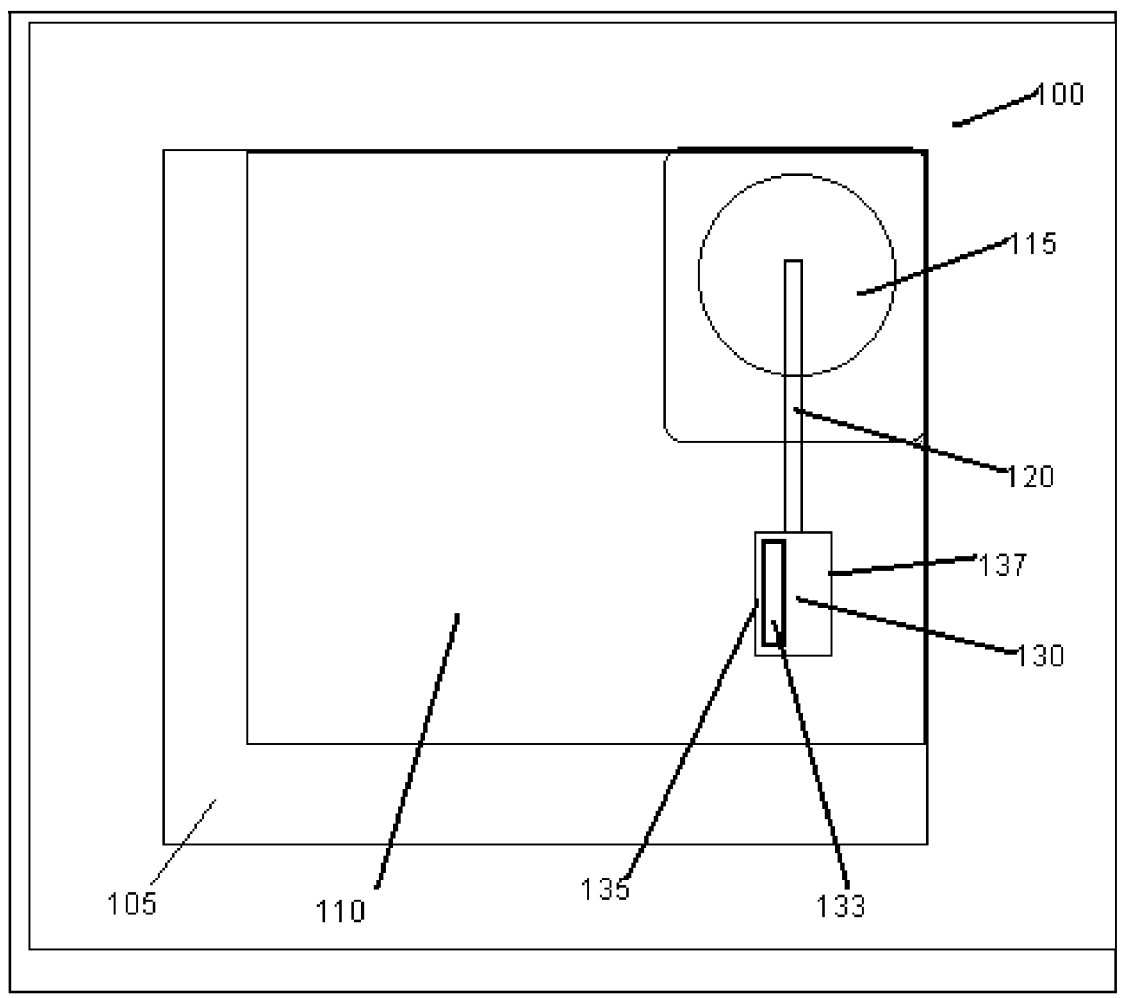
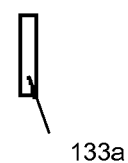
FIG. 3

WET WIPE LOTIONS COMPRISING PARTICULATE MATERIAL

CROSS REFERENCE TO RELATED APPLICATION

This application is a continuation of application Ser. No. 10/941,206, filed Sep. 15, 2004, now U.S. Pat. 7,666,827 the substance of which is incorporated herein by reference.

FIELD OF INVENTION

This invention relates to wet wipes and wet wipe lotions. In particular, to lotions comprising dispersed particulate material. Preferred wet wipes of the invention comprise a substrate material that has been impregnated with the lotion of the invention.

BACKGROUND OF THE INVENTION

Wet wipes, typically a nonwoven material (i.e., a substrate) that is impregnated with a cleaning lotion, are frequently used for personal hygiene tasks such as cleanup after urination or defecation (i. e. perianal cleaning). Wet wipes have found particular utility in helping a caregiver with cleaning tasks related to changing an absorbent article, such as an infant diaper. The cleaning lotion is often an emulsion comprising an oily phase (e. g. an emollient and perfume components), an emulsifier or surfactant and an aqueous phase that comprises further additives such as a rheological modifier. Such lotions facilitate mechanical removal of residues by the substrate by helping to disperse solid matter that is not mechanically removed. Residual lotion components can also provide skin care benefits.

However, improvements are still needed. For example, much of the lotion that is impregnated into the substrate in the manufacturing process is not available to facilitate cleaning. As a result, the wet wipe may also not release enough cleaning lotion to satisfactorily disperse fecal matter. Users of wet wipes react to insufficient lotion negatively. Products that don't deliver enough cleaning lotion are seen as having poor value, having a rough texture so they are harsh (lotion also acts as a lubricant) and not performing well because cleaning is seen as difficult (also seen as resulting from poor lubricity). A particular source of such reduced lotion delivery is lotion drainage from the top of a stack of wet wipes during storage. In this situation, a wipe may be fully saturated immediately after packaging but, with the passage of time, lotion may drain from the wipe and pool in the bottom of the container. As a result, a portion of the wipes, frequently the first wipes encountered when a package is opened, may be drier than is desired for optimal performance.

The art has approached improvement of wet wipe lotion formulation on several fronts: variation of surfactant type and content, variation of emollient type, variation in the preservative system and addition of agents aimed at having an effect on the skin (e.g., botanicals or pharmaceutically active materials). In one example, compositions for non perianal personal cleaning tasks (e.g., removal of dirt, oil and other matter, such as makeup, from the skin or hair) are known. One group of such compositions relies on physical abrasion by suspended particulate matter. However, such products typically are thickened (e.g., in a gel or cream form) and, thus, are not suitable for use with a wet wipe because they have insufficient fluidity to disperse fecal solids that are not mechanically removed by wiping with the wipe. Such thickened compositions also make impregnating the substrate with a cleaning lotion at commercially viable production rates difficult. The art has also considered the balance of ease of lotion impregnation into a substrate and cleaning efficiency by providing lotions with a lower viscosity at elevated temperature (~50° C.) than at room temperature (~25° C.). However, the art has not fully considered the effect of lotion composition on the various requirements a cleaning lotion should satisfy (e. g. ease of lotion impregnation into a substrate, stability of the lotion loading on the substrate during storage and lotion release from the substrate during use).

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures wherein:

FIG. 2 is a schematic view of the apparatus used in the Lotion Release Test.

FIG. 3 is a schematic representation of a clip used in the Lotion Release Test

SUMMARY OF THE INVENTION

Figure 1:
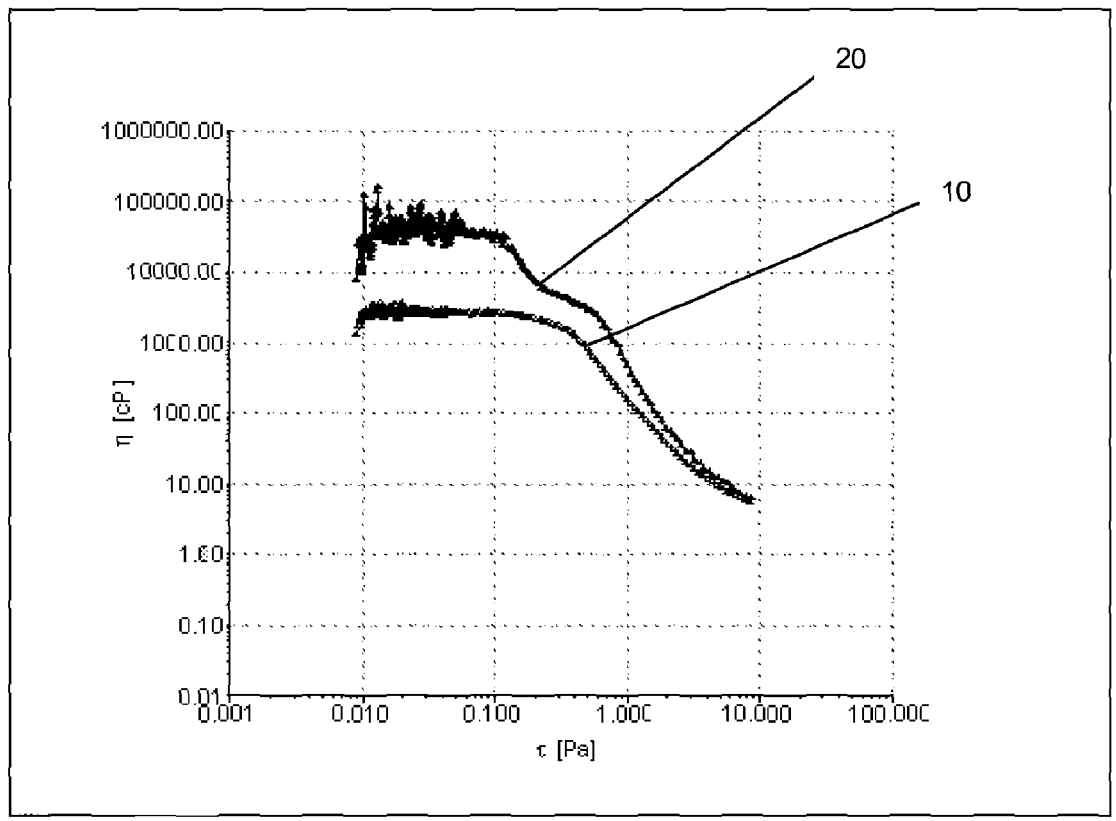
FIG. 1 shows representative shear stress/viscosity curves for a cleaning lotion of the present invention and a prior art cleaning lotion without the added particulate material.

A wet wipe comprising a substrate may impregnated with a cleaning lotion. The cleaning lotion may comprise an emollient, a surface active material, a rheology modifier, and water. The cleaning lotion may further comprise a particulate material at a concentration less than about 2.5%. The cleaning lotion may have:

a. a viscosity less than about 100 centipoise at a shear stress of 10 Pa; and b. a viscosity greater than about 4000 centipoise at a shear stress of 0.05 Pa.

The cleaning lotion may further have a yield value at a shear stress greater than 0.05 Pa.

DETAILED DESCRIPTION OF THE INVENTION

Wet Wipes

The present invention is a wet wipe comprising a cleaning lotion composition where the cleaning lotion composition comprises particulate material.

The term "wet wipe" as used herein refers to a wipe which includes a substrate which is moistened, such as by impregnating the substrate with a liquid cleaning composition, prior to use by the consumer. In particular, "wet wipe" refers to a wipe having a substrate which is impregnated prior to packaging so the wipe is already moist when removed therefrom. Wet wipes, which can also be referred to as "pre-moistened wipes" and "towelettes", are suitable for use in cleaning babies, and can also find use in cleaning tasks related to persons of all ages. Such wipes can also include articles used for application and removal of substances to the body, including but not limited to application and removal of make-up, skin conditioners, ointments, sun-screens, insect repellents, and medications.

As used herein, when used in relation to material compositions the terms "%", "percent", "weight percent" or "percent by weight" refer to the quantity by weight of a component as a percentage of the total, unless indicated otherwise.

As used herein, the terms "emulsifier" or "solubilizer" refer to a component that reduces the tendency of one or more of the components in a lotion composition to separate into an individual bulk phase.

As used herein, the term "particulate material" refers to a component of the cleaning lotion composition that is insoluble/non-molecularly dispersible in an aqueous medium that has a melting point or other first order transition temperature greater than about 80° C. Other important properties of a particulate material are discussed below.

The term "nonwoven" as used herein refers to a sheet, web, or batt of directionally or randomly oriented fibers, bonded by friction, and/or cohesion and/or adhesion, excluding paper, tissue paper, and products which are woven, knitted, tufted, or stitch-bonded. A web is considered to be a paper web, and therefore categorically not included as a web of the present invention, if substantially all of the constituent fibers have a length to diameter ratio less than 300, or a nominal (or average) fiber length of less than about 1 mm. However, a portion of the fibers used to produce nonwoven webs suitable for use as a substrate of the present invention may comprise such relatively short fibers (e.g., fibers derived from a pulping process) if the web also comprises at least a portion of synthetic fibers. An example of webs of this type are those webs comprising an air-formed matrix of thermoplastic polymer microfibers having an average fiber diameter of less than about 10 microns, and a multiplicity of individualized wood pulp fibers disposed throughout the matrix of microfibers and engaging at least some of the microfibers to space the microfibers apart from each other as are described in U.S. Pat. No. 4,100,324.

Substrate

The material used to carry the cleaning lotion (i.e., the "substrate") is generally soft and flexible, potentially having a structured surface enhancing its cleaning performance. The material is preferably a non-woven material, generally comprising at least some synthetic fibers. However, woven materials as well as the use of natural fibers in either woven or nonwoven form are within the scope of the present invention. In one embodiment of the present invention the substrate comprises a non-woven material comprising fibers of a material selected from the group consisting of polyolefins, polyesters, cellulose (including rayon), polyamides, polyesteramides, polyvinyl alcohols, and combinations thereof For the preferred nonwoven materials, any suitable production process may be used including air laying, wet laying, carding, spun bonding and melt blowing and combinations of such production processes. Preferably, the substrate materials are also treated to improve the softness and texture thereof by process such as hydroentanglement or spunlacing.

The substrate should be substantial enough so a user has confidence that it will provide protection against soiling his or her hands during the cleaning process. Suitably, the substrate should have a basis weight of at least about 40 grams/$m^2$. Preferably the substrate has a basis weight of at least about 45 grams/$m^2$. In order to provide value, the substrate basis weight is preferably less than about 100 grams/$m^2$. Particularly preferred substrates have a basis weight between about 45 grams/$m^2$ and about 75 grams/$m^2$, more preferably between about 45 grams/$m^2$ and about 60 grams/$m^2$.

Preferred substrate materials comprise a blend of hydrophilic fibers to insure the substrate is able to imbibe a suitable amount of the cleaning lotion and stiffening fibers to provide a desirable "hand" to the substrate. The substrate may also comprise a layered structure so as to put soft, flexible fibers on the outer surfaces thereof and to "hide" the stiffening fibers in the interior.

A suitable substrate is a carded nonwoven comprising a 40/60 blend of viscose fibers and polypropylene fibers having a basis weight of 58 grams/$m^2$ as is available from Suominen of Tampere, Finland as FIBRELLA 3160. Another suitable material for use as a substrate is SAWATEX 2642 as is available from Sandler AG of Schwarzenbach/Salle, Germany.

Wet wipes are generally of sufficient dimension to allow for a convenient handling. Typically, the substrate is cut and/or folded to such dimensions as part of the manufacturing process. In some instances the substrate is cut into individual portions so as to provide separate wipes which are often stacked and interleaved in consumer packaging. In other embodiments the wipes are in a web form where the web has been slit and folded to a predetermined width and provided with means (e.g., perforations) to allow individual wipes to be separated from the web by a user. Suitably, an individual wet wipe according to the present invention should have a length between about 100 mm and about 250 mm and a width between about 140 mm and about 250 mm. A preferred dimension for a wipe as it is typically used is 200 mm long× 180 mm wide.

Cleaning Lotion

The substrate is generally impregnated with a liquid or semi liquid cleaning lotion, intended to both facilitate cleaning and to provide a smooth feeling to the skin after use. Other ingredients or actives (for example cosmetic actives) can be part of the composition.

Generally the composition is of sufficiently low viscosity to disperse solid soils disposed on the skin and to facilitate impregnation of the entire structure of the wipe. In some other instances, the composition can be primarily present at the wipe surface and to a lesser extent in the inner structure of the wipe. Suitably the substrate is impregnated with at least about 2.0 times its weight with the cleaning lotion. Preferably, the wipe is impregnated with at least about 2.5 times its weight, more preferably with at least about 3.0 times its weight. Alternatively, impregnation to greater than about 6.0 times its weight is undesirable; preferably the substrate is impregnated to less than about 5.0 times its weight.

Desirably, the substrate releasably carries the cleaning lotion, that is, the composition is contained either in or on the substrate and is readily releasable from the substrate by applying a relatively low force to the substrate (e.g., wiping a surface, such as the skin in the perianal area, with the wet wipe). As will be discussed below, the compositions of the present invention provide improved release of the cleaning lotion when compared to compositions that do not comprise particulate materials.

Preferably, when the cleaning lotion of the present invention is loaded onto a substrate the cleaning lotion readily releases therefrom. Suitably a wipe should release at least about 0.3 grams of cleaning lotion when evaluated in the Lotion Release Test described in the TEST METHODS section herein. Preferably, release is at least about 0.35 grams, more preferably release is at least about 0.4 grams.

Alternatively, it is desirable for a wet wipe to release an effective amount of the cleaning lotion that has been impregnated thereinto. Suitably, the wet wipes of the present invention, when evaluated according to the Lotion Release Test release at least about 4% of the impregnated lotion. Preferably the wet wipes release at least about 6%, more preferably at least about 8%. It will be recognized that these relative release values depend on the area of wiping hand 130 and the pressure applied in the Lotion Release Test (discussed below) and an increase in either will result in increased relative release.

The cleaning lotions of the present invention have a non-Newtonian rheological profile. In particular, they have a yield value that provides a high viscosity at low shear and a low viscosity at high shear. Specifically, the cleaning lotions of the present invention have a viscosity at low shear of greater than about 4000 centipoise, preferably greater than about 7000 centipoise, more preferably greater than about 10,000 centipoise at a shear stress of about 0.05 Pascal (Pa) when measured using the shear stress profile using a plate and cone rheometer according to the method described in the TEST METHODS section. Importantly, the lotions of the present invention have at least one yield value which results in a substantial reduction in high shear viscosity for cleaning lotions according to the present invention. As a result the viscosity at a shear stress of 10 Pa (i.e., a shear stress greater than the yield value) for the cleaning lotions of the present invention is substantially reduced (suitably less than about 100 centipoise, preferably less than about 75 centipoise, more preferably less than about 50 centipoise) as measured according to the method described in the TEST METHODS section. Particularly preferred embodiments of the present invention have a yield value less than about 3 Pa so as to provide a substantially reduced viscosity (suitably less than about 100 centipoise, preferably less than about 75 centipoise, more preferably less than about 50 centipoise) at a shear stress of 3 Pa.

It is believed that this non-Newtonian viscosity profile addresses the divergent requirements for a cleaning lotion suitable for wet wipes in a manner that is superior to cleaning lotions previously available. Without being bound by theory it is believed that: 1) the high viscosity at low shear means that the lotions of the present invention have a reduced tendency to drain during product shipment and storage; 2) the low viscosity at higher shear (viscosity typically begins to rapidly decrease at shear stresses less than 1 Pa) means that lotion impregnation is easier (i.e., lotion will readily disperse throughout the substrate during the manufacturing process) and 3) lotion release is improved compared to wet wipes of the prior art.

Representative rheological curves are shown in FIG. 1 where curve 10 is a prior art lotion without particulate material and curve 20 is a cleaning lotion according to the present invention. Without being bound by theory, it is believed that the particulate material of the present invention cooperates with the rheology modifier to provide the collapsible structure that helps maintain a high low shear viscosity so as to minimize drainage of lotion from the substrate while a stack of wipes is in storage (i.e., the particulate material provides added structure that helps maintain a more homogeneous lotion distribution). When comparing curves 10 and 20 it should be noted that the low shear viscosity of the lotion of the present invention (curve 20) is substantially greater than the low shear viscosity of the same lotion composition that contains no particulate material (curve 10). It should be noted that the lotion evaluated to produce curve 10 is substantially similar to cleaning lotions of the prior art. Specifically, the cleaning lotion of the present invention should have a viscosity at 0.05 Pa of more than about 4 times the viscosity of the same lotion composition that has been formulated without additional particulate material (i.e., a viscosity ratio of >4:1), preferably the viscosity ratio is greater than about 6:1, more preferably greater than about 8:1. As noted above, it is believed that this high viscosity ratio is a result of the additional structure in the lotion due to the addition of particulate material.

As will be noted in FIG. 1, the cleaning lotion of the present invention (curve 20) has two yield values. The cleaning lotion first begins to flow at a stress of between about 0.03 and 0.13 Pa and a second viscosity reduction begins at a stress of about 0.3 to about 0.6 Pa. However, such a two yield value structure is not necessary for lotions according to the present invention. For purposes of the present invention, all that is necessary is that the lotion has the non-Newtonian rheology profile described above. For example, a cleaning lotion with a viscosity at shear stress of 0.05 Pa of 5000 centipoise and a viscosity at 3 Pa of 75 centipoise having a yield value at a shear stress between 0.05 Pa and 3 Pa would be a cleaning lotion according to the present invention.

In most of its embodiments, the cleaning lotion of the present invention comprises, but is not limited to: an emollient; a particulate material, a surfactant and/or an emulsifier; a rheology modifier; and water. Other ingredients may be incorporated into the composition, including, but not limited to, soothing agents, botanicals, skin health agents and preservatives. It is to be noted that some compounds can have a multiple function and that all compounds are not necessarily present in the composition of the invention. Preferably, the cleaning composition of the present invention is an oil-in-water emulsion.

Emollient

Common dictionaries define "emollient" as "something that softens or soothes." Emollients are added to wet wipe lotions to provide functionality including but not limited to: (1) improving the glide of the wipe on the skin, by enhancing the lubrication and thus decreasing the abrasion of the skin, (2) hydration of soil residue (for example fecal residue or dried urine residue), thus enhancing their removal from the skin, (3) skin hydration, thus reducing its dryness and irritation while improving its flexibility under the wiping movement, (4) protecting the skin from subsequent irritation (e.g., caused by friction with underwear) as the emollient is deposited onto the skin and remains at its surface as a thin protective layer. As will be recognized, the emollients delivered via the emulsion-based cleaning lotions of the present invention provide such functionalities to a meaningfully greater degree than prior art cleaning lotions that rely only on water soluble emollient materials (e.g., glycerine) in order to provide a low viscosity cleaning lotion for maximum lotion release from the substrate because prior art emulsion-based systems have a higher viscosity resulting in less than optimal lotion release properties.

The emollient of the present invention preferably has a solubility parameter between about 5 and about 12, more preferably between about 5 and about 9.

The amount of emollient that can be included in the lotion composition will depend on a variety of factors, including the particular emollient involved, the lotion-like benefits desired, and the other components in the lotion composition. It has been found that compositions with low or very low emollient content are best suited for the invention: The emollient content of the composition is from about 0.001% to less than about 5%, preferably from about 0.001% to less than about 3%, more preferably from about 0.001% to less than about 2.5% and even more preferably from about 0.001% to less than about 1.5%. Without being bound by the theory, it is believed that a low emollient content decreases the risk of oil/greasy deposit onto the skin so as to minimize negative user perception.

Preferable emollients for use in lotions of the present invention are silicon-based. Silicone-based emollients are organo-silicone-based polymers with repeating silioxane (Si—O) units. Silicone-based emollients of the present invention are hydrophobic and exist in a wide range of possible molecular weights. They include linear, cyclic and cross-linked varieties. Silicone oils are generally chemically inert and usually have a high flash point. Due to their low surface tension, silicone oils readily spread and have high surface activity. Examples of silicon oils suitable for use in the present invention include, but are not limited to: Cyclomethicones, Dimethicones, phenyl-modified silicones, alkyl-modified silicones, silicone resins, and combinations thereof Other emollients useful in the present invention include unsaturated esters or fatty esters, such as ethyl, hexyl stearate or caprylic/capric triglycerides.

A preferred emollient is a combination of bis-PEG/PPG-16/16, PEG/PPG-16/16 Dimethicone with a caprylic/capric triglyceride known as ABILCARE 85 as is available from Degussa Care Specialties of Hopewell, Va. This material is particularly useful because it acts both as an emollient and as an emulsifier.

Particulate Material

An essential component of the cleaning lotions of the present invention is a particulate material. While the cleaning lotions of the present invention can be formulated and converted in a manner similar to currently available cleaning lotions, it has been found that cleaning lotions comprising such materials provide at least two advantages to wet wipes of the present invention: 1) improved release of the lotion from the substrate during the cleaning task and 2) improved skin feel after completion of the cleaning task. Without being bound by theory it is believed that:

The improved release is due to a provision of an increased low shear viscosity due to the inclusion of particulate material as is shown in FIG. 1 and discussed above.

The improved skin feel results from residual particulate material that acts as mini "ball bearings" which provide a lubricious feel to skin that has been cleaned with a wet wipe that comprises the cleaning lotion of the present invention and allowed to dry.

Said another way, the inclusion of the particulate materials described herein provides additional benefits to a wet wipe not previously available to the art.

Only a small amount of particulate material is necessary for the improvement described above. Typically, a cleaning lotion comprising less than about 2.5% particulate material provides improved release compared to a cleaning lotion with no particulate. Preferably, the particulate concentration is less than about 1.5%, more preferably less than about 1.0%. Preferred cleaning lotions have a particulate concentration between about 0.01% and 1.0%. Particularly preferred is a concentration between about 0.4% and 0.6%. Lotions comprising about 0.5% particulate material are especially preferred.

The properties of a suitable particulate material include but are not limited to: insolubility in the liquid phase of the cleaning lotion (even after extended storage), ability of the liquid phase of the cleaning lotion to wet the particulate material, a low enough density and/or a small enough particle size so the particle remains suspended in the liquid phase of the cleaning lotion (as will be recognized, the use of a rheology modifier provides additional flexibility to the density/particle size requirement) and a cost effective performance improvement.

Suitably, the particles have a density between about 0.8 gram/cm$^3$ and about 2.0 gram/cm$^3$. Preferably, the density is between about 0.9 gram/cm$^3$ and about 1.5 gram/cm$^3$. More preferably the density is less than about 1 gram/cm$^3$ so as to minimize particle settling and the density is greater than about 0.9 gram/cm$^3$ so as to minimize particle floatation.

Particles having an mean particle size between about 1 and 100 microns are suitable for use in the present invention. Preferably the mean particle size is less than about 75 microns. A preferred range for mean particle size is between about 5 and about 40 microns. A particularly preferred mean particle size is between about 10 and about 30 microns. Importantly, the particle size distribution should be such that there is a low level of large particles so as to minimize a "gritty" feel during wet wipe use. Suitably, less than 25% of the particles have an equivalent diameter of greater than 100 microns. Preferably less than 25% of the particles have an equivalent diameter of greater than 75 microns.

Suitable commercially available particulate materials include but are not limited to: polyethylene powders are available from Honeywell International of Morristown, N.J. under the trade name ACUMIST; polymethyl methacrylate microspheres as are available from KOBO of South Plainfield, N.J. as BPA; lactone cross polymer microspheres as are available from KOBO as BPD; nylon 12 microspheres as are available from KOBO as NYLON SP; polymethylsilsesquioxane microspheres as are available from KOBO as TOSPEARL; cellulose microspheres as are available from KOBO as CELLO-BEADS; silica microspheres as are available from KOBO as MSS; polytetrafluoroethylene powders as are available from Micro Powders, Inc. of Tarrytown, N.Y. as MICROSLIP; micronized waxes as are available from Micro Powders as MICROEASE; blends of natural wax and micronized polymers as are available form Micro Powders as MICROCARE and microspherical particles of a copolymer of vinylidene chloride, acrylonitrile and methylmethacrylate available as EXPANCEL from Expancel, Inc. of Duluth, Ga. Preferred are polyolefin powders as are available from Equistar Chemical Corp. Houston, Tex. as MICROTHENE. Particularly preferred is MICROTHENE FN510-00 from Equistar.

Emulsifier/Surfactant

The cleaning lotion also includes one or more emulsifiers as are known in the art for forming oil-in-water emulsions. Preferred emulsifiers are those that also perform well as a surfactant to aid in cleaning. Mixtures of emulsifiers and other surface active components may also be used. The emulsifier can be a polymeric emulsifier. Surfactants/emulsifiers providing the cleaning lotion with a low surface tension are preferred for the present invention. Importantly, the emulsifier must help insure that the liquid phase of the cleaning lotion has a surface tension lower than the surface energy of the particulate material so as to enable wetting of the particulate material therewith. Other characteristics of preferable surfactant/emulsifier include high polarity and a non-ionic nature.

Particularly preferred emulsifiers are nonionic surfactants. Examples of nonionic surfactants are disclosed in McCutcheon's, Detergents and Emulsifiers, North American Edition (1997) and McCutcheon's, Functional Materials, North American Edition (1997) both published by Mc Publishing Co. of Glen Rock, N.J.

Nonionic surfactants useful herein include those selected from the group consisting of alkyl glycosides and alkyl polyglycosides. These can be broadly defined as a condensation product of a long chain alcohol, e.g. $C_8$-$C_{30}$ alcohols, with a sugar; a sugar polymer or a starch (i.e., a glycoside or a polyglycoside). These compounds can be represented by the formula $(S)_n$—O—R wherein S is a sugar moiety such as glucose, fructose, mannose, and galactose; n is an integer of from about 1 to about 1000, and R is a $C_8$-$C_{30}$ alkyl group. Non-limiting examples of an alkyl glycoside and an alkyl polyglycoside include polysorbate-20 and polysorbate-60.

Also useful are ethoxylated and propoxylated alcohol ethers; ethoxylated and propoxylated esters; and ethoxylated and propoxylated amides. These can be broadly defined as condensation products of long chain alcohols or carboxylic acids or amides, e.g. $C_8$-$C_{30}$ alcohols or $C_8$-$C_{30}$ carboxylic acids or $C_8$-$C_{30}$ carboxylic acid amides, with an alkoxide such as ethylene oxide and/or propylene oxide.

Also useful are ethoxylated and propoxylated mono-, di-, and tri-glycerides. These can be broadly defined as condensation products of long-chain carboxylic acids (e.g., $C_{8-30}$ carboxylic acids) with glycerin where either one or two or three carboxylic acid moieties are bound to the glycerin moiety. Non-limiting examples include PEG-40 hydrogenated castor oil from BASF of Ludwigshafen, Germany as Cremophor C-40 or PEG-6 Caprylic/Capric Glycerides from Sasol Germany GmbH of Witten, Germany as Softigen-767.

Also useful are silicone co-polyol surfactants. These can be broadly defined as condensation products of ethylene oxide and/or propylene oxide and poly-dimethylsiloxane. These materials can adopt a number of structures, including but not limited to linear structures, and pendant structures. Non-limiting examples include Bis-PEG/PPG-16/16 PEG/PPG-16/16 Dimethicone; Bis-PEG/PPG-20/20 PEG/PPG-20/20 Dimethicone; PEG/PPG-20/6 Dimethicone; and PEG/PPG-4/12 Dimethicone as are available from Degussa Care Specialties of Hopewell, Va. under the trade name ABIL and the silicone glycol copolymers as are available from GE Silicones of Wilton, Conn. under the trade name SILWET L.

Also suitable are glycerol esters and alkoxylated derivatives thereof. Exemplary materials include the glyceryl stearate blends available from Degussa Care Specialties of Hopewell, Va. under the name TEGO CARE.

Also useful are ionic surfactants including anionic surfactants, amphoteric surfactants and zwitterionic surfactants.

Particularly suited for the present invention are emulsifiers such as alkylpolylglycosides (e.g., Polysorbate 20 available from Uniqema of New Castle, Del.) and a blend of caprylic capric triglyceride and bis-PEG/PPG-16/16 PEG/PPG-16/16 dimethicone (ABILCARE 85 from Degussa Care Specialties of Hopewell, Va.) and combinations thereof. ABILCARE 85 is especially preferred because heating the aqueous phase is not necessary for emulsion formation and because the blend also provides emollient functionality.

The emulsifier is employed in an amount effective to emulsify the emollient and other non-water-soluble oils that may be present in the composition with enough surface active material still available to facilitate the cleaning task. The cleaning lotion preferably comprises less than about 3 percent of the nonionic surfactant. More preferably, the lotion can comprise less than about 1 percent of the nonionic surfactant. Even more preferably, the lotion comprises between about 0.3 and about 0.6 percent by weight of the nonionic surfactant. In some instances compositions may comprise more than one emulsifier (i.e., an emulsifier and a co-emulsifier). In such compositions, the total concentration of components that are effective emulsifiers is preferably less than about 3 percent, more preferably less than about 2 percent, still more preferably less than about 1.5 percent.

In one embodiment of the present invention, the concentrated composition has a ratio between the amount of surfactant and the emollient amount between about 9:1 and about 1:72 (on a weight/weight basis), more preferably between about 6:1 to about 1:30 (w/w).

Rheology Modifier

It has been found that the rheology of the composition plays a significant role in its functionality. A series of compounds aimed at insuring the desired rheology have been found to be preferable. These compounds are also called stabilizers for their role in the stabilization of the composition.

Rheology modifiers are compounds that increase the viscosity of the composition at lower temperatures as well as at process temperatures. Rheology modifiers or suspending agents or stabilizers also provide "structure" to the compositions to prevent settling out (separation) of insoluble and partially soluble components. Other components or additives of the compositions may affect the temperature viscosity/rheology of the compositions.

The effect and advantage of rheology modifiers are in particular described in US Patent Application Serial No. 20020128621A1 entitled "Absorbent articles with simplified compositions having good stability" published on Sep. 12, 2002, filed on Dec. 21, 2001, by Kruchoski et al., and US Patent Application Serial No. 20020128615A1 entitled "Absorbent articles with non-aqueous compositions containing anionic polymers" published on Sep. 12, 2002, filed on Dec. 22, 2001, by Tyrrell et al.

In addition to stabilizing the suspension of insoluble and partially soluble components, the rheology modifiers of the invention also help to stabilize the composition on the wipe and enhance the transfer of lotion to the skin: The wiping movement increases the shear and pressure therefore decreasing the viscosity of the lotion and enabling a better transfer to the skin as well as a better lubrication effect.

Additionally, the rheology modifier helps to preserve a homogeneous distribution of the composition within the wipe stack: Any fluid composition has a tendency to migrate to the lower part of the wipes stack during prolonged storage. This effect creates an upper zone of the stack having less composition than the bottom part. This is seen as a sign of relatively low quality by the users.

Preferred rheology modifiers exhibit low initial viscosity and high yield. Particularly suited for the present invention are rheology modifiers such as, but not limited to:

Blends of material as are available from Uniqema GmbH&Co. KG, of Emmerich, Germany under the trade name ARLATONE. Particularly preferred are ARLATONE V-175 which is a blend of Sucrose Palmitate, Glyceryl Stearate, Glyceryl Stearate Citrate, Sucrose, Mannan, and Xanthan Gum and ARLATONE V-100 which is a blend of Steareth-100, Steareth-2, Glyceryl Stearate Citrate, Sucrose, Mannan and Xanthan Gum.

Blends of materials as are available from Seppic France of Paris, France as SIMULGEL. Particularly preferred are SIMULGEL NS which comprises a blend of a hydroxyethylacrylate/sodium acryloyldimethyl taurate copolymer with squalane and polysorbate 60 and SIMULGEL EPG which comprises a blend of a sodium acrylate/sodium acryloyldimethyltaurate copolymer with polyisobutene and caprylyl capryl glucoside.

Acrylate homopolymers, acrylate crosspolymers, such as but not limited to Acrylate/C10-30 alkyl acrylate crosspolymers, carbomers, such as but not limited to acrylic acid cross linked with one or more allyl ether, such as but not limited to allyl ethers of pentaerythritol, allyl ethers of sucrose, allyl ethers of propylene, and combinations thereof as are available as the Carbopol® 900 series from Noveon, Inc. of Cleveland, Ohio (e.g., Carbopol® 954).

Naturally occurring polymers such as xanthan gum, Galactoarabinan and other polysaccharides.

Combinations of the above rheology modifiers.

Examples of commercially available rheology modifiers include, but are not limited to, Ultrez-10, a carbomer; Pemulen TR-2, an acrylate crosspolymer; both of which are available from Noveon, Cleveland OH and Keltrol, a xanthan gum, available from CP Kelco San Diego, Calif.

Rheology modifiers, when present may be used in the present invention at a weight/weight % (w/w) from about 0.01% to about 3%, preferably from about 0.015% to about 2%, more preferably from about 0.02% to about 1%.

Other Optional Components of the Cleaning Lotion

The cleaning lotions of the present invention can optionally include an adjunct ingredient. The adjunct ingredient may include a wide range of additional ingredients such as, but not limited to perfumes, fragrances, preservatives, rheology modifiers, moisturizers, texturizers, colorants, medically active ingredients, in particular healing actives and skin protectants. Combinations of adjunct ingredients are also within the scope of the present invention.

Humectants are hygroscopic materials that function to draw water into the stratum corneum to hydrate the skin. The water may come from the dermis or from the atmosphere. Examples of humectants include glycerin, propylene glycol, and phospholipids.

Fragrance components, such as perfumes, include, but are not limited to water insoluble oils, including essential oils.

Preservatives prevent the growth of micro-organisms in the liquid lotion and/or on the substrate. Generally, such preservatives are hydrophobic or hydrophilic organic molecules. Suitable preservatives include, but are not limited to parabens, such as methyl parabens, propyl parabens, alkyl glycinates, iodine derivatives, quaternary ammonium salts (e.g., benzalkonium chloride) and combinations thereof. Particularly preferred preservative systems are disclosed in published US Pat. Application No. 2004/022158 and in U.S. patent application Ser. No. 10/878,875.

Method of Production

The cleaning composition may be formed by combining the components as described below to form an emulsion. Alternatively, the composition and wipes are made according to copending U.S. Provisional Patent Application No. 60/520032. In one embodiment, the cleaning lotion may be prepared by dilution of a concentrated composition that has a water content of less than about 30%, preferably the water content is less than about 20%, more preferably less than about 10%. The minimum amount of water is, in most embodiments of the concentrated composition, greater than about 0.1%. Such a preparation scheme has the advantage of minimizing the quantity of material (particularly water) that needs to be heated during the emulsification process. The need for high shear process equipment is also minimized because the amount of material that is processed by such high shear equipment is also minimized Examples of concentrated compositions that do not contain particulate material according to the present invention are described in co-pending U.S. Provisional Pat. Application No. 60/520031. A suitable method of preparing such concentrated compositions is discussed below.

Converting

A suitable process to produce the wipes of the present invention comprises a step of providing a wipe substrate and delivering a quantity of the cleaning lotion to the substrate. This step is referred to as a converting step. Any suitable substrate as described above can be used in the converting step, preferably, however, the substrate comprises a hydroentangled carded web made up of a blend of polypropylene and cellulosic fibers. The step of impregnating the substrate with the cleaning lotion can be achieved by any conventional application process, such as (but not limited to) submersion, spraying, padding, extrusion coating and dip coating. Particularly preferred for commercial production is extrusion coating where the cleaning lotion is applied to a moving web of substrate at the desired add-on rate from an extrusion header (similar to a slot coater). Alternatively, a suitable number of dry portions of substrate that have been cut and folded to suitable dimensions may be placed in a container and a suitable quantity of the composition may be delivered to the container so as to impregnate the substrate during finished product shipment.

Article of Commerce

In one embodiment of the present invention an article of commerce is provided. The article of commerce of the present invention typically comprises (a) a container as described herein, and (b) at least one wet wipe as described herein.

Containers useful in the present article include but are not limited, for example, PET tubs, flow wrap pouches, precut sachets for individually packed wipes, and other packaging known in the art as suitable Test Methods Lotion Release Test This method is intended to determine the release of cleaning lotion from a wet wipe upon wiping a wet wipe over a defined area, using defined pressure and speed.

Apparatus and Materials

Wiping Apparatus: A suitable apparatus 100 is shown in FIG. 1. The apparatus comprises:

Plate 105 A plate (40 cm×40 cm×15 mm) comprising polyacetal (e.g., DELRIN from DuPont of Wilmington, Del. is suitable;

Drive Mechanism 115 Able to cause rotation of wiping hand through an angle of 100° and a linear velocity of 15 cm/sec at the center point of the wiping hand 130, a drive mechanism from a windshield wiper, such as Part No. 058745-0390242401, CDP 24 volt from Bosch Automotive Karlsruhe, Germany, has been found to be suitable;

Arm 120 An aluminum bar stock (20 mm×7 mm), flexibly coupled (e.g., via universal joints) to drive mechanism 115 at one end and the center of wiping hand 130 at the other end so as to provide a 211 mm radius of rotation and to allow lifting of wiping hand 130 above the plane of plate 105;

Wiping Hand 130 Plate 18 cm×8 cm with sufficient weight to provide a wiping pressure of 827 Pa (0.12 psi).

Channel 133 A channel (170 mm×17 mm×7 mm deep) is milled into the top surface of wiping hand 130 adjacent the leading edge 135 thereof This channel provides a recess that works in cooperation with clip 133a (a rectangular solid sized slightly smaller than channel 133 so as to provide a friction fit to hold a wipe sample in place without tearing the wipe sample) to allow temporary attachment of a wipe sample.

Balance: A balance accurate to ±0.001 g such as the Model PR2003 Delta Range from Mettler-Toledo, Inc. of Columbus, Ohio or equivalent is suitable.

Skin Analog: A polypropylene film available as DC Fix Foil 200-0907 from Konrad Hornschuch AG, Weissbach, Germany is used. The analog is cut to dimensions of 45 cm×40 cm. Shown as 110 in FIG. 1 (Position as shown on FIG. 1).

Test Procedure: The test may be suitably carried out in a constant temperature/humidity room set to the following: 25° C.-29° C.; Relative Humidity 35%-45%.

1) Take one wipe out of the pack and record its initial weight (AWW).
2) Attach the wipe to the wiping hand 130 by placing one edge thereof on the top surface of hand 130 so that it overlies the inboard edge of channel 133. Place clip 133a (a rectangular solid sized slightly smaller than channel 133 so as to provide a friction fit to hold a wipe sample in place without tearing the wipe sample) into channel 133 on the top surface of the wipe sample to temporarily attach the wipe to hand 130. Wrap the wipe around wiping hand 130 smoothing any wrinkles. The edge of the wipe opposite to the edge placed under clip 133a is brought around the trailing edge 137 and adhered to hand 130 by the capillary forces provided by the cleaning lotion.
3) Operate drive mechanism 115 so as to cause hand 130 to rotate through a 100° arc at a linear velocity of 15 cm/sec.
4) Repeat Step 4 for 3 cycles. If drive mechanism 115 is a windshield wiper mechanism hand 130 can be allowed to reciprocate for three cycles, otherwise, lift arm 120 and return hand 130 to the starting position so as to cycle 3 times.
5) Remove the wipe from the wiping hand 130 and record the end weight (PWW).
6) Clean the skin analog with deionized water and dry with tissue.
7) Perform the next measurement.
8) Repeat steps 2-8 for 5 wipes.

Calculation and Report

Lotion Load=(AWW-SW)/SW where:

SW: Sheet weight dry—Measured by washing at least 3 representative wipes with deionized water to remove any cleaning lotion and drying the washed wipes overnight at room temperature. SW is the average weight of the three washed wipes.

Weight Loss=AWW-PWW

Weight Loss [%] of Lotion Load=(WL*100)/LL

Report the average and standard deviation of, lotion load, weight loss and weight loss as a percent of lotion load. If desired, standard statistical techniques (e.g., analysis of variance, Tukey-Kramer comparison of means and the like) can be used to evaluate the raw data to compare wet wipe samples having different compositions.

Rheometry

This method is suitable for determination of the yield value (i.e., the shear stress at which apparent viscosity begins to reduce) of neat cleaning lotions and cleaning lotions expressed from saturated wet wipes.

Apparatus

| | |
|---|---|
| Rheometer | A Haake model RS600 Rheometer as is available from Thermo Haake (or equivalent) of Paramus, NJ is suitable |
| Cone Plate - 60 mm 1° Ti | Haake Part No. 222-1273 |
| Base Plate - for 60 mm sensor | Haake Part No. 222-1298 |
| Constant Temperature Bath | Any model capable of maintaining 22° ± 1° C. accuracy. |
| Data Acquisition and Analysis Software | Rheo Win Pro. Version 296 is suitable for operation of the Haake instrument or equivalent software suitable for use with instruments should be used. |
| Personal Computer | Any computer capable of running the RheoWin software |

Procedure

This procedure is suitable for setup and operation of the Haake instrument. It should be modified as necessary by a skilled rheometer so as to provide equivalent results if another instrument is used.

Preparation of Equipment

1. The Haake rheometer geometry and inertia will be calibrated during initial installation and set up by the manufacturer.
2. Consult the owner's manual for further information concerning the operation of both the rheometer and the constant temperature bath.
3. Equilibrate the constant temperature bath to 22° C.±1° C.
4. Load the 60 mm base plate by pressing the plate straight down against the spring force of the temperature sensor and turning counter clockwise. This ensures proper seating of the plate. Tighten the threaded connection to attach the 60 mm cone to the rheometer.
5. Turn on the personal computer and open the RheoWin Pro Job Manager software.
6. Confirm the following setup parameters are entered:

| Parameter | Value |
|---|---|
| a) Temperature | a) 22° C. |
| b) Cont Stress, Stress Sweep Graphic Defn. | b) |
| c) Controlled Stress Controlled Rotation Ramp | c) Select: Start τ = 0.0 Pa, End τ = 10.0 Pa, Distribution = log, Duration = 200 Seconds, Acquisition # data = 400, break shear rate > 100 sec$^{-1}$, |
| d) Zero Point Measurement Position | d) Select from Axial Parameters Zero Point Menu: Find and Set Zero Point and Prompt Message When Finished "Load Sample" Select from Axial Parameters/Measurement Position: Go to measurement position, speed-max and, from standby submenu: 2 mm |
| e) Lift Apart | e) Select Move Lift Apart from Axial Parameter Sub menu; Enter Prompt "Clean off Sensor and save file" under Axial Options Submenu |
| f) Devices | f) 60 mm Cone Plate |
| g) Display | g) Mode = Auto |
| h) Filename | h) Select: Ask for File Name and At end of job |
| i) Segments | i) Select: All Segments under subheading save segments |
| j) Max Time | j) 300 seconds |

Instrument Operation

7. The job is now properly set up and the rheometer is ready to run. Make sure that the cone plate sensor and the base plate are clean. (isopropanol or ethanol are suitable cleaning aids). Allow the sensor and base plate to dry.
8. Click Start at the bottom of the job window. The rheometer will zero itself. The base plate will move to reach the parallel plate sensor (top) and automatically zero. When the machine has successfully zeroed itself, a message "Load sample" will appear on the screen.
9. Using a pipette or equivalent, place approximately 1.15 ml of product on measuring plate. Click OK for load sample. Insure the sample is deposited close to the center of the plate to help assure that the entire gap between the plate and the cone is filled when the apparatus is in a closed configuration.

10. The rheometer will slowly close. When the gap setting is reached, a message box will appear "Ready to run". Click OK.
11. The test will now run automatically.
12. When the test is complete, a message "Test Finished" will appear on the screen. Click OK. The computer will then prompt the operator to "Save as". Save file appropriately.
13. The rheometer will automatically open. Unscrew the cone plate from the instrument. Clean both the sensor and base plate with a clean lint-free laboratory wipe and isopropanol or ethanol. Allow the cone and base plate to dry before running the next sample.

Analysis of Data
1. Open the RheoWin Pro Data Manager software. Open the file containing the run data. A data table with information on the side will appear.
2. From the main menu select Layout, Graph Layout, and the Controlled Stress Sweep Template. Click OK. A graph will appear with stress or Tau as the x axis and shear strain on the y axis. If desired, this template may be modified to show apparent viscosity ($\eta$) on the y axis.
3. Click the icon at the top of the menu bar which shows $\tau_0$ or yield stress. Select the data and click calculate as new. This yield point evaluation tool performs a curve analysis where the point of deformation or where the curve bends is considered the yield point. The yield point will then be displayed. Alternatively, the intersection of extrapolated line from the relatively horizontal portion of a graph of $\eta$ vs. t with a line extrapolated from the declining portion of the graph will define the approximate yield value.

Particle Size Distribution

This method is intended to determine the particle size distribution of particulate material in a wet wipe cleaning lotion. The method makes use of a laser diffraction particle size analyzer (e.g., the Horiba LA-910) for particle size measurement.

Particulate Material Separation
1. From a tub of wipes or a refill package, remove one wipe from the top, middle, and bottom of the stack. Cut each wipe into four equal-sized strips and place the strips for each wipe into separate 200 ml polypropylene centrifuge bottles (such as VWR Catalog No. 21020-500 from VWR International of West Chester, Pa.).
2. Add 100 ml of 70:30 ethanol:distilled water solution to each centrifuge bottle. Place each centrifuge bottle into the clamp of a wrist action shaker (such as VWR Catalog No. 57039-055) and shake vigorously (-200 rpm) for 10 minutes.
3. Remove the centrifuge bottles from the shaker and let stand upright for 5 minutes. Remove the cap of each bottle and, using clean forceps, gentle remove the strips of substrate and discard.
4. Replace the caps onto each centrifuge bottle and place each bottle into a table top centrifuge (such as VWR Catalog No. BK366802). Centrifuge the bottles at 4000 g for 10 minutes at 20° C.
5. Carefully aspirate off the upper liquid, being careful not to disrupt the pellet.
6. Wash the pellet by adding 100 ml of 70:30 ethanol:distilled water, replacing the bottle cap, and agitating vigorously with a vortex mixer (such as VWR Catalog No. 12620-838). This step is intended to remove any remaining oily components of the lotion, surfactants, rheology modifier, and the like from the particulate material.
7. Pellet the washed particulates by centrifuging at 7000 g for 10 minutes at 20° C.
8. Repeat step 5.
9. Resuspend the pelleted particulate material in 5 ml of 70:30 ethanol/distilled water by gently sucking the beads up and down into a plastic 25 ml polystyrene serological pipette (such as VWR Catalog No. 20171-044).
10. Analyze for particle size distribution.
11. Repeat steps 1-10 an additional 5 times.

Particle Size Distribution Determination

This method is suitable for measuring the particle size distribution of a solid material (e.g., the disperse phase of an emulsion or other particulate material) that is dispersed in an aqueous medium.

Device Details and Settings
Device: Horiba LA-910 as is available from Horiba Europe GmbH of Sulzbach/Ts., Germany The device should be set up and operated according to the manufacturer's instructions. Standard setup conditions:

| Standard setup conditions: | |
|---|---|
| Agitation speed | 2 |
| Circulation speed | 1 |
| Ultra Sonic speed | 1 min 0 |
| Sonic Works during Measuring | NO |
| Waiting time after Ultra Sonic | 0 sec |
| Sampling times | 15 |
| Form of distribution | Standard |
| Type of Dispersant | Deionized water |
| Relative Refractive Index | Enter the refractive index of the particulate material and set the suspending fluid compensation factor to 0.00 (i). |

Operation
1. Partially fill (200-250 ml) the sample cup with deionized water.
2. Start device control software (File name is "Measure") on the computer that controls the Horiba device and turn on the agitator and recirculation systems.
3. Confirm system cleanliness by conducting a "Blank" particle size measurement.
4. Add the sample to be tested dropwise using a disposable pipette (A suitable pipette is available from VWR International of West Chester, Pa. as Catalog No. 73990-114). Continue adding sample until the transmission (magenta bar) and backscatter (blue bar) indicator bars are in the green range of the display of the attached computer. This indicates that the particulate concentration in the sample chamber is high enough for a reliable measurement.
5. Instruct the control software to conduct a particle size measurement. When the measurement is complete the display will show a report that includes a curve representing the particle size distribution and characteristics of the distribution (e.g., mean particle size). This report can also be printed.
6. Repeat steps 1-5 for each sample.

Report
Report the average and standard deviation of the mean particle size for each sample.

Particulate Material Concentration

This method is intended to determine the concentration of particulate material in a wet wipe cleaning lotion.

Method
1) Weigh a 50 ml polypropylene centrifuge tube (e.g., Catalog No. 20171-028 as available from VWR International of West Chester, Pa.) accurately to ±0.001 grams and record the empty weight as $Wt_{1,i}$ where "i" is the sample number.

2) Accurately weigh 10.00±0.01 grams of the lotion extracted using the method described for particle size distribution determination into the weighed centrifuge tube. Record the filled tube weight as $Wt_{2i}$.
3) Separate the particulate material as described in the particle size distribution test method above. Wash the separated material by agitating vigorously with a vortex mixer (such as VWR Catalog No. 12620-838).
4) After the water washing step place the sample (with cap loosened) in a vacuum oven and dry overnight at 60° C. at a pressure of $1 \times 10^{-3}$ torr.
5) Weigh the dried sample. Record the dried weight as $Wt_{3i}$
6) Repeat steps 1-5 for 4 additional aliquots of the extracted cleaning lotion for total of 5 replicates.

Calculation and Report
1) For each sample, particulate material concentration can be determined as follows: % Particulate Material$_i$=100× $(Wt_{3i}-Wt_{1t})/Wt_{2t}-Wt_{1t})$
2) Report the mean and standard deviation for each wipe lotion tested.

Examples

Example 1

This example is intended to demonstrate formulation of cleaning lotions with and without particulate material according to the present invention.

| | Composition | |
|---|---|---|
| Ingredient | A Concentration (%) | B[5] Concentration (%) |
| Water | QS | QS |
| MICROTHENE FN510-00[1] | 0.5 | — |
| CREMOPHOR[4] | 0.80 | 0.80 |
| Decyl glucoside | 0.05 | 0.05 |
| ABILCARE 85[2] | 0.45 | 0.45 |
| KELTROL[3] | 0.2 | 0.2 |
| Preservative | 1.95 | 1.95 |

[1]Polyethylene microbeads from Equistar Chemical Corp. of Huston, TX
[2]85:15 bis-PEG/PPG-16/16 PEG/PPG-16/16 dimethicone:capric-caprylic triglyceride from Degussa Care Specialties of Hopewell, VA
[3]Xanthan gum available from CP Kelco US of Wilmington, DE
[4]PEG-40 Hydrogenated Castor Oil available from BASF of Ludwigshafen, Germany
[5]Composition according to Provisional U.S. patent application Ser. No. 60/520,031.

Preparation
1. Weigh out water and start mixing. A mixer rotating in the range of 2000-3000RPM is used. A suitable mixer for laboratory batches is made by Charles Ross and Son Company of Hauppauge, N.Y. as model ME-100 LC.
2. Add the EDTA and mix until fully dissolved for about 2 to 10 minutes.
3. Add the KELTROL and mix for about 1 hour.
4. Prepare a premix of 90 parts of Abilcare 85 and 10 parts of decyl glucoside as follows. Weigh both the ABILCARE 85 and the decyl glucoside into the cup of a SpeedMixer Model DAC 150 FVV-k (available from Flacktech, Inc. of Landrum, S.C.). Start the mixer up and operate it for one minute at 3500 rpm to blend the materials.
5. While agitating the blend of water, EDTA and KELTROL, add 0.50% of this premix to the batch and continue mixing for about 10 minutes.
6. Make a premix containing 71 parts of the preservative system and 29 parts of Cremophor. Mix until homogeneous
7. Add the preservative/Cremophor premix while continuing to agitate the batch and mix for about 30 minutes.

Lotion was applied to the substrate as follows:
1. Three sheets of dry substrate were stacked, weighed and immersed in the requisite amount of cleaning lotion (based on sheet weight).
2. A hand roller was used to evenly distribute the lotion throughout the sheets.
3. The saturated substrate samples were stored in a ZIPLOC bag until they were evaluated for mechanical properties in order to prevent drying. A 4.5 kg weight was placed on the closed bag (after air is expelled therefrom) to aid in ply-to-ply contact.
4. Steps 1 through 3 were repeated with additional groups of three sheets until sufficient substrate was treated for the testing described below. Newly treated substrates were added to the stack of treated substrates in the bag as more substrate sheets are treated.

Example 2

This example is intended to demonstrate the lotion release of wet wipes impregnated with the cleaning lotions of Example 1.

Table 1 shows lotion release data for the products of Example 1.

TABLE 1

| Evaluation Test | A[1] | B[2] |
|---|---|---|
| Lotion Release (g) | 0.44 | 0.26 |

[1]Cleaning lotion of the present invention
[2]Prior art cleaning lotion

As can be seen, the cleaning lotion of the present invention makes more lotion available for the cleaning task.

Example 3

This example is intended to demonstrate formulation of alternative cleaning lotions with and without particulate material according to the present invention.

| | Composition | |
|---|---|---|
| Ingredient | C[6] Concentration (%) | D Concentration (%) |
| Water | QS | QS |
| MICROTHENE FN510-00[1] | — | 0.5 |
| CREMOPHOR[4] | 0.8 | 0.8 |
| Plantacare 2000[5] | 0.05 | 0.05 |
| ABILCARE 85[2] | 0.45 | 0.45 |
| KELTROL[3] | 0.2 | 0.2 |
| Preservative | 1.95 | 1.95 |
| Anhydrous Disodium EDTA | 0.10 | 0.10 |

[1]Polyethylene microbeads from Equistar Chemical Corp. of Huston, TX
[2]85:15 bis-PEG/PPG-16/16 PEG/PPG-16/16 dimethicone:capric-caprylic triglyceride from Degussa Care Specialties of Hopewell, VA
[3]Xanthan gum available from CP Kelco US of Wilmington, DE
[4]PEG-40 Hydrogenated Castor Oil available from BASF of Ludwigshafen, Germany
[5]Decyl glucoside as is available from Cognis Corp. of Cincinnati, OH.
[6]Composition according to Provisional U.S. patent application Ser. No. 60/520,031.

Composition C was prepared as follows:
Preparation
1. Weigh out water and start mixing. A mixer rotating in the range of 2000-3000RPM is used. A suitable mixer for laboratory batches is made by Charles Ross and Son Company of Hauppauge, N.Y. as model ME-100 LC.
2. Add the EDTA and mix until fully dissolved for about 2 to 10 minutes.
3. Add the KELTROL and mix for about 1 hour.
4. Prepare a premix of 90 parts of Abilcare 85 and 10 parts of decyl glucoside as follows. Weigh both the ABILCARE 85 and the decyl glucoside into the cup of a SpeedMixer Model DAC 150 FVV-k (available from Flacktech, Inc. of Landrum, S.C.). Start the mixer up and operate it for one minute at 3500 rpm to blend the materials.
5. While agitating the blend of water, EDTA and KELTROL, add 0.50% of this premix to the batch and continue mixing for about 10 minutes.
6. Make a premix containing 71 parts of the preservative system and 29 parts of Cremophor. Mix until homogeneous.
7. Add the preservative/Cremophor premix while continuing to agitate the batch and mix for about 30 minutes.

Lotion was applied to the substrate as follows:
1. Three sheets of dry substrate were stacked, weighed and immersed in the requisite amount of cleaning lotion (based on sheet weight).
2. A hand roller was used to evenly distribute the lotion throughout the sheets.
3. The saturated substrate samples were stored in a ZIPLOC bag until they were evaluated for mechanical properties in order to prevent drying. A 4.5 kg weight was placed on the closed bag (after air is expelled therefrom) to aid in ply-to-ply contact.
4. Steps 1 through 3 were repeated with additional groups of three sheets until sufficient substrate was treated for the testing described below. Newly treated substrates were added to the stack of treated substrates in the bag as more substrate sheets are treated.

Example 4

This example is intended to show user perception of wipes impregnated with the cleaning lotions of Example 3.

Wet wipes impregnated with one of cleaning lotions C or D were shown to a small group of adult females. When the group was questioned about their perceptions of the wet wipes, they reported that the initial skin feel of the wipes impregnated with a cleaning lotion comprising the particulate materials of the present invention (Composition D) was wetter than the initial skin feel of wipes impregnated with a cleaning lotion that did not contain the particulate material (Composition C).

Example 5

This example is intended to demonstrate the effect of another particulate material. In summary, a lotion composition substantially similar to the compositions described in Examples 1 and 3 was prepared using polymethylsilsesquioxane microspheres (TOSPEARL 145A, from KOBO). The specific formulation prepared is given below.

| Ingredient | Composition Concentration (%) |
| --- | --- |
| Water | QS |
| TOSPEARL 145A[1] | 2.00 |
| TEGOSOFT CT[2] | 2.00 |
| MONTANOV L[4] | 1.80 |
| DC 200[5] | 2.00 |
| KELTROL[3] | 0.25 |
| Preservative | 2.25 |
| Anhydrous Disodium EDTA | 0.10 |
| Perfume | 0.06 |

[1]Polymethylsilsesquioxane microspheres available from KOBO of South Plainfield, NJ
[2]Capric-caprylic triglyceride from Degussa Care Specialties of Hopewell, VA
[3]Xanthan gum available from CP Kelco US of Wilmington, DE
[4]Blend of $C_{14-22}$ fatty alcohol and $C_{12-20}$ alkylglucoside available form Adinop Co., Ltd. of Bangkok, Thailand
[5]Dimethicone 200 Fluid ® (200 cs available from Dow Corning of Midland MI The composition is prepared as follows:
1. Disperse the KELTROL in cold water-phase with a high shear mixer (An Ultra Turrax Model T50 available from IKA® Works, Inc. of Wilmington, N.C. is suitable) at high speed until the gum is completely hydrated.
2. Heat the water dispersion to about 75° C. and add the MONTALEV L. Continue heating until the MONTALEV is completely dissolved.
3. Add the EDTA and the preservative system to heated water phase with the high shear mixer at high speed, continue mixing until completely dissolved
4. Continue mixing for further 3 minutes
5. Add the TEGOSOFT with the high shear mixer at high speed and mix for an additional 3 minutes.
6. Allow the aqueous phase to cool to 60° C.
7. Premix the DC 200 Fluid® and the TOSPEARL using a propeller mixer, until the particles are visibly fully dispersed.
8. Add this premix to the 60° C. aqueous phase with the high shear mixer at high speed, and mix for 3 minutes
9. Replace the high shear mixer with a propeller mixer having a speed range of between about 50 and about 2000 rpm.
10. Allow the blend to cool to 40° C. with continued agitation by the propeller mixer.
11. Add the perfume at 40° C. with the agitator at high speed (250 rpm) and mix for 3 minutes
12. Continue stirring with the agitator at approx. 150-200 rpm until the emulsion has reached 30° C.
13. Mix the finished batch with the agitator at moderate speed for further 20 minutes.

Rheometry measurements on this lotion shows the following:

| Measured Property | Result |
| --- | --- |
| Viscosity at 0.05 Pa Shear Stress (centipoise) | 8000 |
| Yield Value (Pa) | 1.79 |
| Viscosity at 10 Pa Shear Stress (centipoise) | 60 |

All documents cited in the Detailed Description of the Invention are, in relevant part, incorporated herein by reference; the citation of any document is not to be construed as an admission that it is prior art with respect to the present invention.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising a substrate that has been impregnated with a cleaning lotion, the cleaning lotion comprising an emollient, a surface active material, a rheology modifier and water, the cleaning lotion further comprising a particulate material at a concentration less than about 2.5%, and the cleaning lotion has:
   a. a viscosity less than about 100 centipoise at a shear stress of 10 Pa; and
   b. a viscosity greater than about 4000 centipoise at a shear stress of 0.05 Pa.

2. A wet wipe according to claim 1 wherein the viscosity is greater than about 7000 centipoise at a shear stress of 0.05 Pa.

3. A wet wipe according to claim 1 wherein the viscosity is less than about 75 centipoise at a shear stress of 10 Pa.

4. A wet wipe according to claim 1 wherein the viscosity is less than about 100 centipoise at a shear stress of 3 Pa.

5. A wet wipe according to claim 1 wherein the particulate material has a mean particle size between from about 1 and about 75 microns.

6. A wet wipe according to claim 3 wherein the particulate material has a mean particle size between from about 5 microns and about 40 microns.

7. A wet wipe according to claim 4 wherein the particulate material has a mean particle size between from about 10 microns and about 30 microns.

8. A wet wipe according to claim 1 wherein the particulate material concentration is less than about 1.5%.

9. A wet wipe according to claim 6 wherein the particulate material concentration is less than about 1.0%.

10. A wet wipe according to claim 8 wherein the particulate material concentration is between from about 0.01% to about 1.0%.

11. A wet wipe according to claim 1 wherein the particulate material is selected from the group consisting of polyolefin powders, polymethyl methacrylate microspheres, lactone cross polymer microspheres, nylon microspheres, polymethylsilsesquioxane microspheres, cellulose microspheres, and mixtures thereof.

12. A wet wipe according to claim 11 wherein the particulate material is selected from the group consisting of polyolefin powders, polymethylsilsesquioxane microspheres and mixtures thereof.

13. A wet wipe according to claim 1 wherein the wet wipe has a lotion release greater than about 0.3 grams.

14. A wet wipe according to claim 1 wherein the wet wipe has a relative lotion release greater than about 4.0%.

15. A wet wipe according to claim 1 wherein the particulate material has a mean particle size between from about 1 to about 100 microns.

16. A wet wipe according to claim 4 wherein the particulate material has a density from between about 0.8 gram/cm$^3$ to about 2.0 gram/cm$^3$.

17. A wet wipe according to claim 1 wherein the particulate material has a density between from about 0.9 gram/cm$^3$ to about 1.5 gram/cm$^3$.

18. A wet wipe according to claim 1 wherein the particulate material has a density less than about 1 gram/cm$^3$ and greater than about 0.9 gram/cm$^3$.

19. A wet wipe according to claim 1 wherein the particulate material is a microsphere.

20. A wet wipe comprising a substrate that has been impregnated with a cleaning lotion, the cleaning lotion comprising an emollient, a surface active material, a rheology modifier and water, the cleaning lotion further comprising a particulate material at a concentration less than about 2.5%, and the cleaning lotion has:
   a. a viscosity less than about 100 centipoise at a shear stress of 3 Pa; and
   b. a yield value at a shear stress greater than 0.05 Pa.

* * * * *